(12) United States Patent
Hartman et al.

(10) Patent No.: US 6,779,215 B2
(45) Date of Patent: Aug. 24, 2004

(54) POWER TOOTHBRUSH

(75) Inventors: Frederick R. Hartman, Englishtown, NJ (US); Luiz Arthur Bonaci Tessarotto, Plainsboro, NJ (US); Raymond J. Hull, Jr., Hampton, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 240 days.

(21) Appl. No.: 10/109,176

(22) Filed: Mar. 28, 2002

(65) Prior Publication Data

US 2003/0182745 A1 Oct. 2, 2003

(51) Int. Cl.7 ............................................... A61C 17/34
(52) U.S. Cl. ...................................................... 15/22.1
(58) Field of Search ........................................ 15/22.1

(56) References Cited

U.S. PATENT DOCUMENTS

| | | | |
|---|---|---|---|
| 2,917,758 A | 12/1959 | Held et al. | ..................... 15/22.1 |
| 3,046,584 A | 7/1962 | Wepfer | |
| 3,278,963 A | * 10/1966 | Bond | ......................... 15/22.1 |
| 3,538,359 A | * 11/1970 | Barowski | ..................... 310/29 |

FOREIGN PATENT DOCUMENTS

EP          0 968 686 A     1/2000

* cited by examiner

*Primary Examiner*—Mark Spisich (57) ABSTRACT

A power toothbrush has an elongated body defining a handle and containing a power source, a stepper motor and an electronic controller; an elongated housing having bristles at the end thereof, and structure for operatively connecting the output shaft of the stepper motor to the housing. The stepper motor provides rotary oscillating motion which is transmitted to the housing which carries the bristles.

1 Claim, 12 Drawing Sheets

POWER TOOTHBRUSH

BACKGROUND OF THE INVENTION

1. Field of the Invention

This invention relates to a power toothbrush having a bristle head coupled to a drive shaft. The drive shaft, and hence the bristle head coupled thereto, undergoes rotary oscillating motion about the axis of the drive shaft. The rotary oscillating motion is provided by a stepper motor. "Rotary oscillating motion" is sometimes referred to in the art as "angular displacement" or "sweep angle".

2. Description of the Prior Art

To many people, the prevention of cavities in teeth is of utmost importance. The most common treatments for preventing cavities include brushing the teeth, flossing, and using fluoride rinses. Of these treatments, brushing the teeth is most common. Manual toothbrushes have dominated the toothbrush market for many years. Recently, power toothbrushes have increased in sales. The implication is that power toothbrushes may clean the teeth better than manual brushes.

Several varieties of power toothbrushes are sold commercially. The toothbrushes are typically powered by a motor which, in turn, is powered by a battery. In some instances, the batteries are re-chargeable. The motion of the toothbrush bristle head may vary. In a first design, the bristle head comprises a circular disk on which are mounted, generally parallel to the central axis of the disk, a plurality of bristles or bristle tufts. In one aspect of this first design, this bristle head is adapted to undergo continuous rotation about its central axis during use of the toothbrush. In a second aspect of this first design, the bristle head is adapted to undergo repeating partial rotation about its central axis, i.e., the bristle head travels a limited distance along an arc of a circle in one direction (for example, counterclockwise) after which the bristle head travels along the same arc in the opposite direction (for example, clockwise).

In a second design, the bristle head comprises a base which is generally rectangular in configuration and has a longitudinal axis. The bristle head base carries bristles or bristle tufts which are secured perpendicularly to its surface and are usually arranged in longitudinally extending rows. In a first aspect of this second design, the bristle head is adapted to undergo continuous reciprocating motion whereby the bristle head moves forward and backward alternately in a direction parallel to its longitudinal axis. In a second aspect of said second design, the bristle head is adapted to undergo oscillating motion about its longitudinal axis, i.e., the bristle head, when viewed in front end elevation, moves in a back-and-forth, arcuate path in the fashion of a pendulum. Such motion is also referred to as rotary oscillation motion.

There is a continuing effort to provide power toothbrushes that clean teeth better. The term "cleaning teeth better" means cleaning the surface of the teeth better, cleaning between the teeth better, cleaning behind the teeth better, or some combination thereof.

European Patent Application 0 968 686 teaches a power toothbrush with a toothbrush head that has oscillating motion about its longitudinal axis, i.e., rotary oscillating motion. A relatively complex transmission assembly is utilized to convert the rotational movement of an output shaft of a motor into rotary oscillating motion at the bristle head of the toothbrush.

It would be advantageous to have a power toothbrush having a bristle head which undergoes rotary oscillating motion, which said oscillating motion is provided by either a simplified transmission assembly or with no transmission assembly at all.

SUMMARY OF THE INVENTION

The present invention provides a power toothbrush comprising:

an elongate body defining a handle and having an interior cavity formed therein, said elongate body having a distal end and a proximal end;

an elongate housing having a proximal end and a distal end, said housing including a plurality of bristles at its distal end;

a stepper motor disposed within the interior cavity of the elongate body, said stepper motor including an output shaft providing rotary oscillating motion; and means for operatively connecting said elongate housing to the output shaft of said stepper motor.

In one embodiment of the present invention, the end portion of the output shaft of the stepper motor has a rectangular cross-section and the elongate housing comprises a matching rectangular slot at its end. The elongate housing and the stepper motor output shaft are operatively connected by inserting the output shaft having the rectangular cross-section into the rectangular slot of the elongate housing. It will be understood by those skilled in the art that other cross-sectional configurations could be employed. For example, the output shaft could be triangular in configuration and the elongate body would have a triangular slot at its distal end to receive the triangularly shaped stepper motor output shaft in operative engagement.

In a second embodiment of the present invention, the output shaft of the stepper motor is connected, by a coupling mechanism, to a connector shaft which extends beyond the distal end of the elongate body. The connector shaft in turn is secured to the elongate housing comprising the toothbrush bristle arrangement. In use, the rotary oscillating motion of the output shaft of the stepper motor is transmitted, via the coupling mechanism, to the elongate housing comprising the aforementioned toothbrush bristle arrangement whereby the bristle arrangement undergoes the same rotary oscillating motion as the output shaft of the stepper motor.

In each of the aforementioned embodiments, the stepper motor may be controlled by electronic controller means which regulates the motion of the output shaft of the aforementioned stepper motor. In other words, the electronic controller means is operatively connected to the stepper motor and controls that motor in such fashion that the output shaft thereof is provided with the desired rotary oscillating motion.

The power toothbrushes of the present invention may further include means for insuring that the desired rotary oscillating motion, i.e., sweep angle, of the stepper motor output shaft is achieved at start-up or is maintained or restored in the event excessive force is applied to the toothbrush during use.

DETAILED DESCRIPTION OF PREFERRED EMBODIMENTS

The power toothbrushes of the present invention comprise an elongate body having a proximal end and a distal end. The elongate body defines a handle portion for gripping the power toothbrush and has an interior cavity formed therein which extends from its proximal end to its distal end. The elongate body may be made of any material suitable for power toothbrush bodies. Such materials include, but are not limited to, polyolefins, such as polyethylene and polypropylene; polycarbonate; polyurethanes; polyesters such as polyethylene terephthalate, polybutylene terephthalate, and polycaprolactone; polyamides, such as nylon 6 and nylon 12; cellulose acetate propionate; styrene acrylonitrile copolymers; alkyl benzyl styrene copolymers; and the like. The elongate body may be made by any process known in the art, such as injection molding, machine forming, and stamping. Injection molding is particularly useful.

As indicated earlier herein, the elongate body defines a handle and has an interior cavity formed therein. The interior cavity holds a source of energy for the motor, such as a battery. Solar cells or fuel cells may also be utilized as energy sources. Any conventional battery may be utilized as the energy source. The battery may be re-chargeable. The battery may be re-charged by removing the battery from the toothbrush and connecting the battery to a re-charging station, as is known in the art. Alternatively, the battery may be left in the toothbrush and the toothbrush placed in a suitable re-charging station for recharging of the battery.

An elongate housing having a proximal end and a distal end is operatively connected to the output shaft of the stepper motor and includes a toothbrush bristle head at the distal end thereof. The elongate housing may be designed to provide the power toothbrush with a neck portion which is angled. If an angled neck portion is provided, the angle of the toothbrush neck may range from about 5° to about 20°, preferably from about 12° to about 20°. The toothbrush bristle head may be detachably connected or permanently connected to the elongate body. Mechanisms for detachably or permanently attaching toothbrush heads to elongate bodies are well known in the art. The elongate housing and toothbrush head may be made of the same materials and by the same processes as those used to make the elongate body.

In embodiments of the present invention which comprise a connector shaft operatively connected at its proximal end to the output shaft of the stepper motor and at its distal end to the elongate housing comprising the toothbrush bristle head, the connector shaft may be made of any suitable material, such as, but not limited to, the materials described above for the elongate body, or metals, such as stainless steel and the like.

The connector shaft may be operatively connected to the elongate housing carrying the toothbrush bristle head and to the output shaft of the stepper motor by any suitable coupling means known in the art. Such coupling means include, but are not limited to, rubber tubing, a flexible angular misalignment coupler, a universal joint, and a flexible shaft drive coupling. Such couplings are commercially available through, for example, Guardian Company under the GUARDEX tradename, through KTR company under the ROTEX tradename, or through Rimtec Corporation. The couplings and other parts of the power toothbrush may be coated with silicone, polytetrafluoroethylene, or the like to reduce friction between cooperating parts.

The size of the couplings will vary depending on, for example, the size of the elongate drive shaft, the size of the rotating output shaft, and the size of the toothbrush head.

In one embodiment of the present invention, a stepper motor having an output shaft adapted or controlled to provide oscillatory motion is disposed within the interior cavity of the elongate body. Such motors are commercially available and are known for use in other arts. Stepper motors suitable for use in the present invention include, but are not limited to, those available through Arsape Company, Mototech Incorporated, and Phytron Company. The stepper motor may be a direct drive motor, or may have a built in mechanical torque converter. The stepper motor may have a rotational motion on the output shaft and simple mechanical torque converters that convert the motion of the motor into rotary oscillating motion about the axis of the drive shaft. The axis of rotation of the toothbrush head is coaxial with the handle. The rotation of the toothbrush head is parallel to the surface of the teeth. Useful stepper motors include unipolar and bipolar stepper motors. The stepper motors may have up to 5 phases. The stepper motors may be operated at frequencies ranging from about 5 Hz to about 30 Hz, preferably from about 6 Hz to about 20 Hz. The output shaft of the stepper motor may be made of the same materials as listed for the elongate drive shaft above.

An electronic controller may be provided to control the motor. In embodiments where rechargeable batteries are utilized, the electronic controller regulates re-charging the battery. The electronic controller may also be utilized to control automatic shut off timers or audible signal timers. The electronic controller may be any device known in the electrical art for controlling the flow of power. Such devices include, but are not limited to, integrated circuits, resistors, capacitors, transistors, and zenners or diodes.

The toothbrush head has a multiplicity of bristles. The bristles may be on a flat platform toothbrush head or a toothbrush head having a circular cross-section. Alternatively, the bristles may be radially outwardly projecting from the toothbrush head. The bristle arrangement may include tufts, individually embedded bristles, or combinations thereof. The bristles may have different profiles and different colors. The bristles may be held in place by means known in the art, such as stapling or fusion.

A shroud that partially surrounds the toothbrush head may be utilized. As is known in the art, a shroud may be formed integral with the toothbrush head to enclose a portion of the toothbrush head. Alternatively, the shroud may be molded separately and may be attached to the toothbrush head, for example through a snap on fit. The shroud prevents toothpaste from spraying away during use of the toothbrush. The shroud may also protect the cheeks and gums of the user from undesired contact with the bristles.

The power toothbrush may include a timer with or without an audible signal that the teeth have been brushed for a sufficient time. Alternatively, the timer may provide an automatic shut off for the power toothbrush after the teeth have been brushed for a sufficient time. Means for controlling the timer and automatically shutting off the power toothbrush or providing an audible signal include, but are not limited to, the use of a computer chip, the use of an integrated circuit, the use of transistors, and the use of resistors. The audible signal may be a beep, music, and the like.

The combination of the motor, the elongate drive shaft, and the connecting means provides the toothbrush head with a rotational angular displacement. The angular displacement may range from about 10° to about 60°, for example, from about 30° to about 60°.

BRIEF DESCRIPTION OF THE DRAWINGS

The present invention will be more readily understood by reference to the appended drawings in which.

One preferred embodiment of a power toothbrush in accordance with the teachings of the present invention is illustrated in FIGS. 1–9 of the appended drawings. Toothbrush 10 comprises an elongate body 15; an elongate housing 30; a stepper motor 50 having an output shaft 52; an electronic controller 45; a power source 40 for the stepper motor; and means for operatively connecting said elongate housing to the output shaft of the stepper motor.

Elongate body 15 has a proximal end 16 and a distal end 17. Elongate body 15 comprises a handle portion 18 extending from its proximal end; an elongated, reduced diameter portion 22 terminating at distal end 17, and a tapered neck portion 20 intermediate handle 18 and elongated, reduced diameter portion 22. Body 15 comprises an interiorly located cavity 24 which is closed at proximal end 16 by closure cap 26. In the embodiment under discussion, closure cap 26 has a hollow tubular portion 26b and a slightly enlarged base portion 26a. End cap 26 is held in place within the distal end of cavity 24 by a friction fit. Alternatively, closure cap 26 may be threaded into cavity 24. As can be seen by reference to FIG. 2, power source 40, preferably a battery, is disposed within hollow tubular portion 26b of end closure 26.

Figure 2:
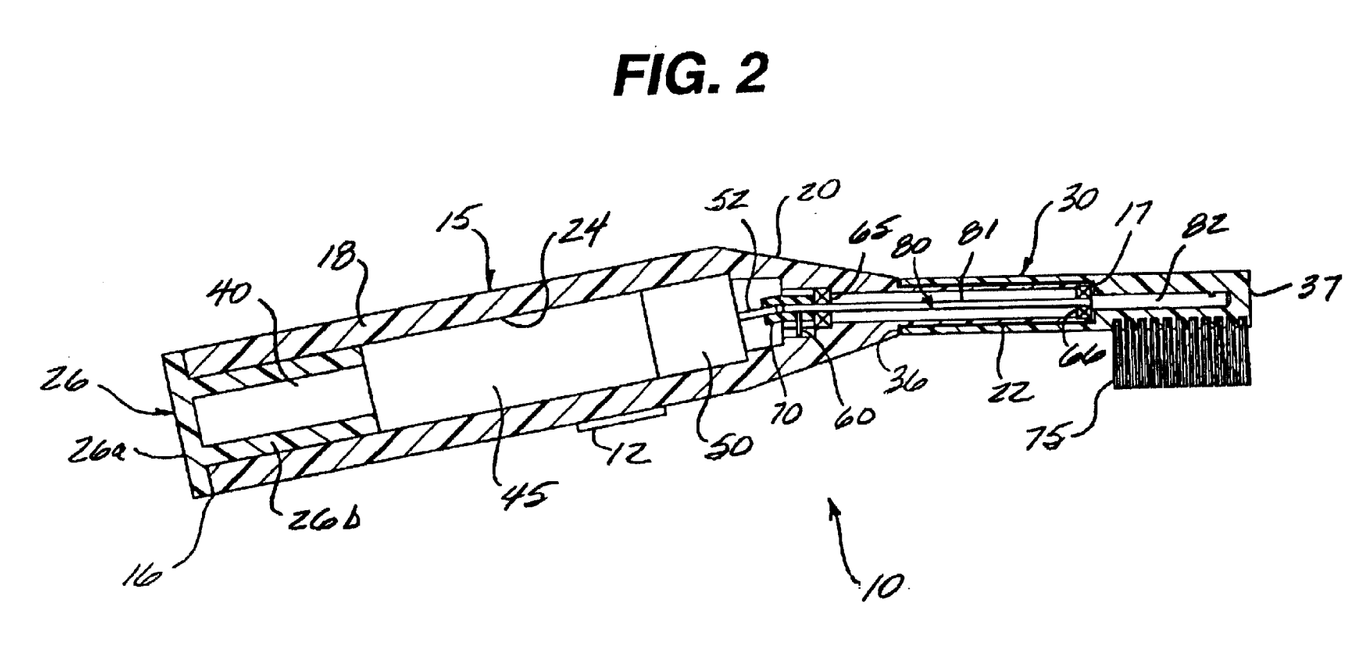
FIG. 2 is a longitudinal cross-section, with some portions shown schematically, of the toothbrush of FIG. 1.

Controller means 45 and stepper motor 50 are disposed within cavity 24 in the manner shown in FIG. 2, with the stepper motor being located toward the distal end of handle 18 and the controller means being located between the power source 40 and stepper motor 50.

Stepper motor 50 has an output shaft 52 which is regulated by controller means 45 to have the above-described rotary oscillating motion.

Elongated housing 30, which comprises an interiorly located cavity 31, is open at its proximal end 36 and closed at its distal end 37. Cavity 31 comprises a proximal cavity portion 33 and a distal cavity portion 34, each of said cavity portions being substantially circular in cross-section. Cavity portion 33 is sized so as to fit over elongated, reduced diameter portion 22 of body 15 with enough clearance therebetween to allow housing 30 to move with respect to reduced diameter portion 22. The diameter of distal cavity portion 34 is smaller than the diameter of proximal cavity portion 33.

Figure 2A:
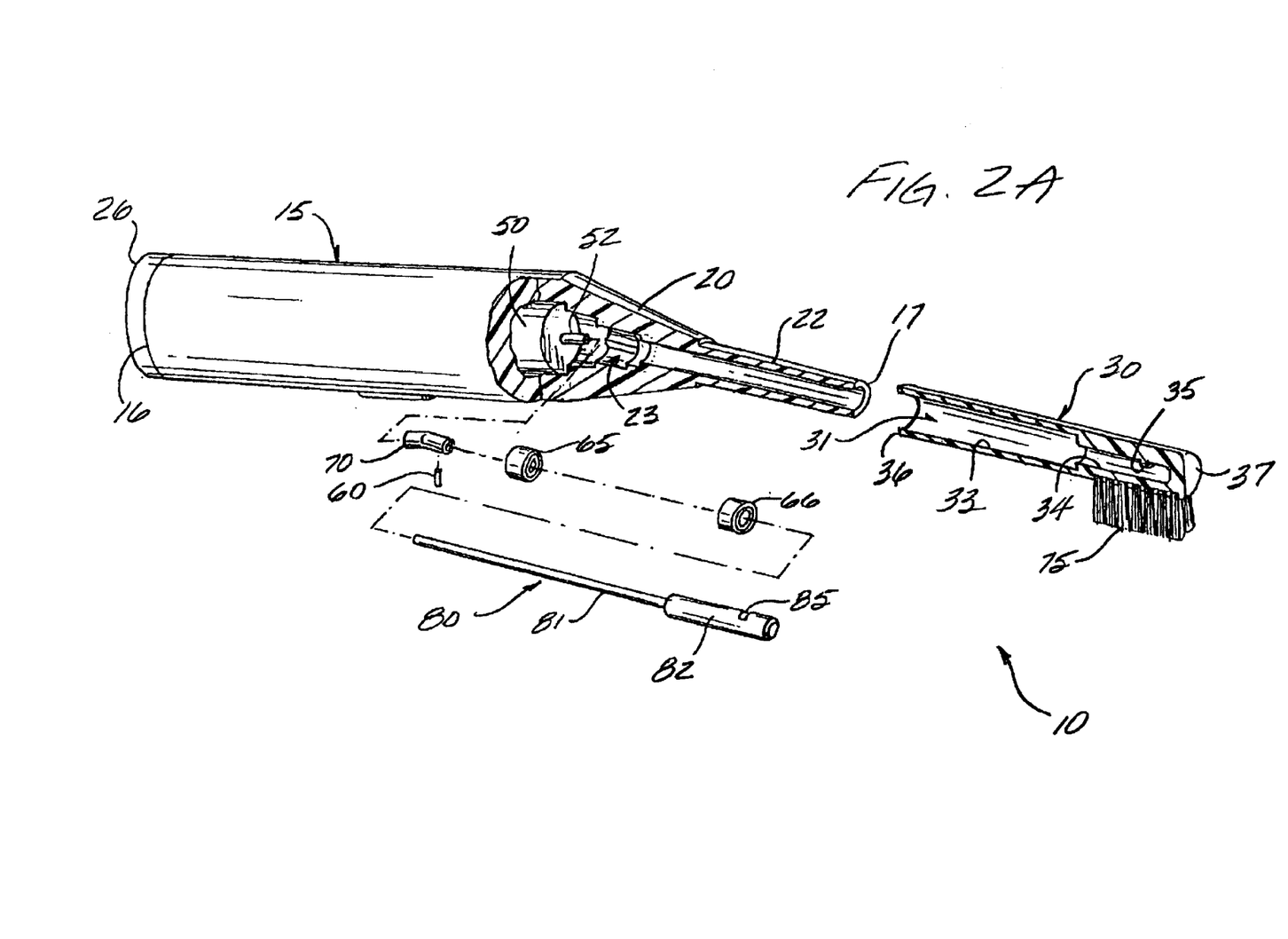
FIG. 2A is an exploded perspective view, with some portions shown in section, of the toothbrush of FIG. 1.
Figure 2B:
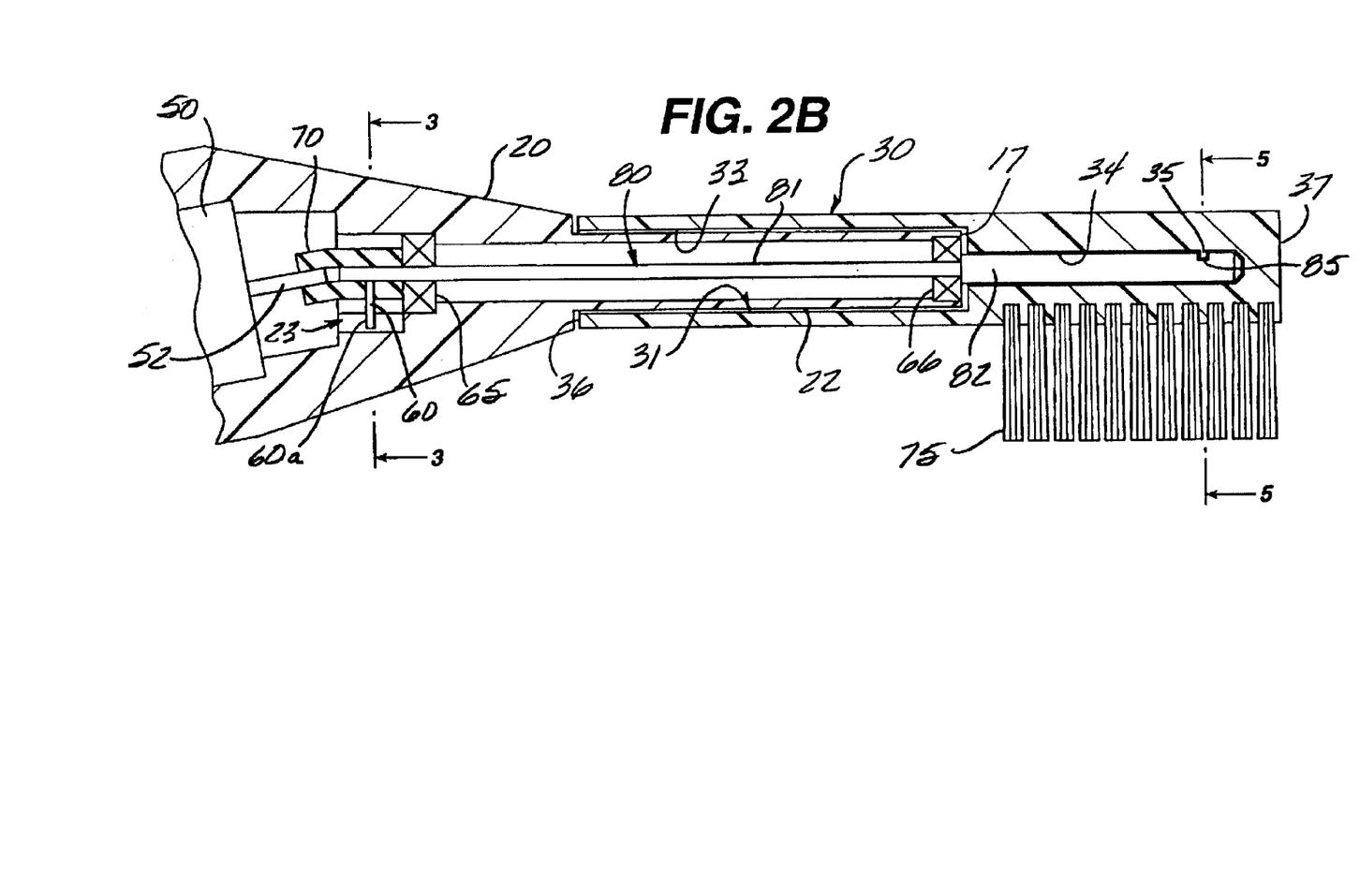
FIG. 2B is an enlarged longitudinal cross-section of the distal portion of the toothbrush of FIG. 1.

In the preferred embodiment under discussion and as seen in FIGS. 2, 2A and 2B, the output shaft 52 of stepper motor 50 is operatively connected to elongated housing 30 by coupling means comprising a flexible connector 70 and an elongated connecting shaft 80. As seen in the Figures, the distal end of output shaft 52 is connected to the proximal end of elongated connecting shaft 80 by aforementioned flexible connector 70. The flexible connector, as mentioned earlier herein, may comprise, e.g., rubber tubing, a flexible misalignment coupler, a universal joint, a flexible shaft driving coupling, or the like. Connecting shaft 80, which may be made of metal or plastic, comprises distal portion 82 and reduced-diameter proximal portion 81. The proximal portion of shaft 80 is mounted in bearings 65 and 66 as seen in FIG. 2B. The distal portion of shaft 80 comprises a notch 85 formed in a portion of its peripheral surface. Notch 85 engages with a rib 35 formed in a portion of the interior wall of elongated housing 30. In the assembled configuration seen in FIG. 2B, notch 85 is releasably engaged with rib 35 to thereby operatively attach shaft 80 to housing 30. When the toothbrush is in operation, the motion of output shaft 52 is thus transmitted to housing 30 and the desired rotary oscillating motion is imparted to toothbrush bristles 75.

A conventional slidable power switch or push button switch 12 is provided on the elongate body for controlling the operation of the toothbrush. A battery 40 is located within the interior cavity. Conductive wires connect the battery and the motor to the power switch so that power can be transferred from the battery to the motor. An electronic controller 45 is provided to control the operation of the motor. In embodiments where rechargeable batteries are utilized, the controller also regulates re-charging of the battery. The electronic controller may also be utilized to control automatic shut off timers or audible signal timers. The electronic controller may be any device known in the electrical art for controlling the flow of power. Such devices include, but are not limited to, integrated circuits, resistors, transistors, and zenners or diodes.

Figure 3:
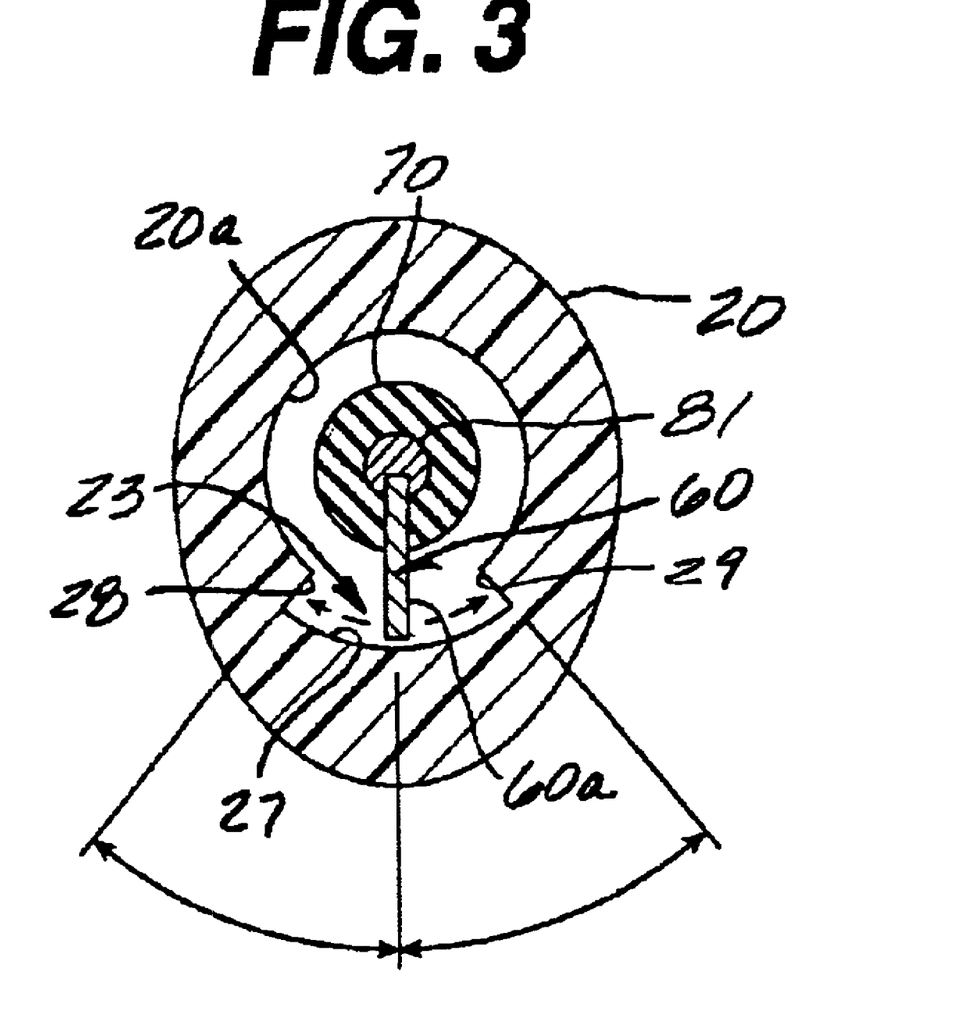
FIG. 3 is a cross-sectional view taken along line 3—3 of FIG. 2.
Figure 4A:
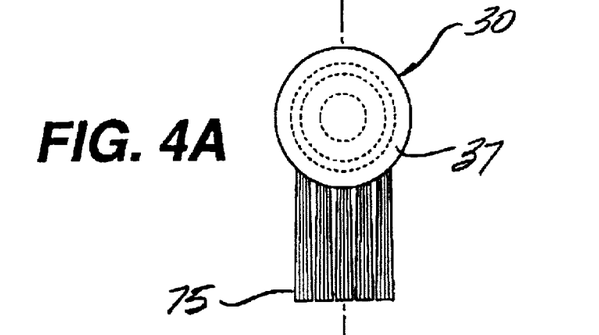
FIG. 4A is a schematic front-end view taken along line 4A—4A of FIG. 1.
Figure 4B:
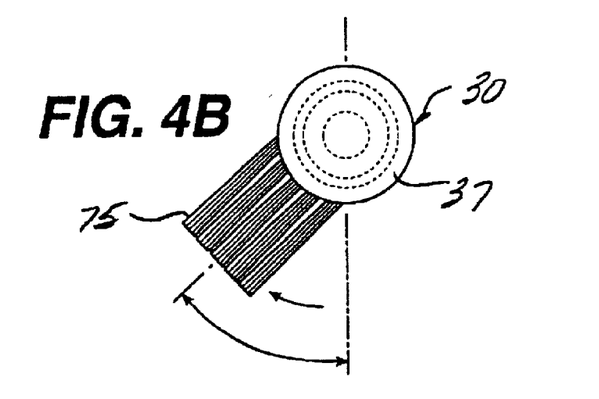
FIGS. 4B and 4C are views similar to FIG. 4A and illustrating the rotary oscillating motion of the elongate body and its associated bristle head during use of the toothbrush.
Figure 4C:
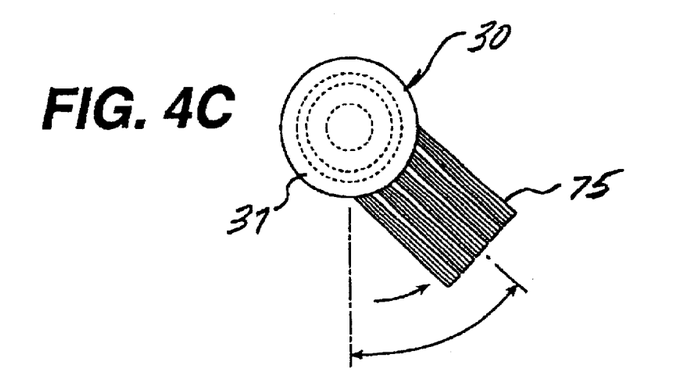
Figure 5:
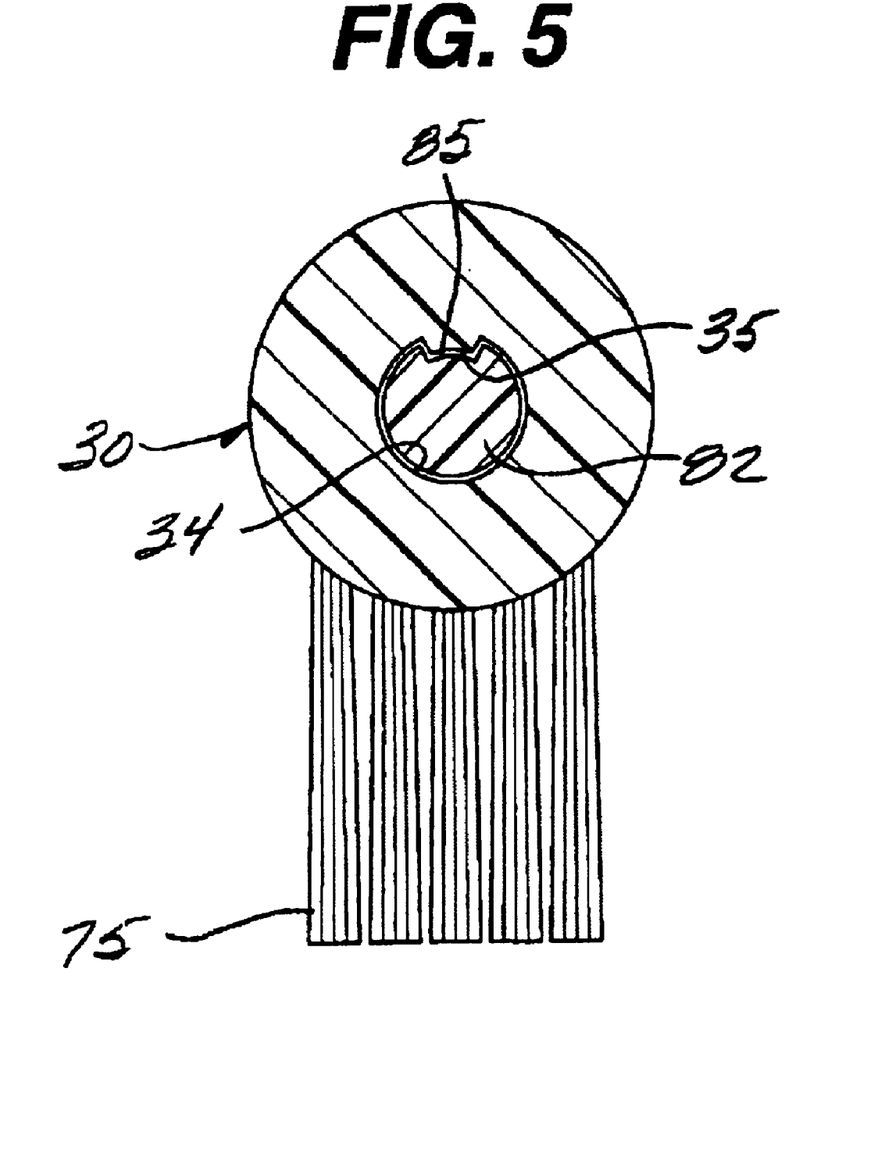
FIG. 5 is a cross-sectional view taken along line 5—5 of FIG. 2B.
Figure 6:
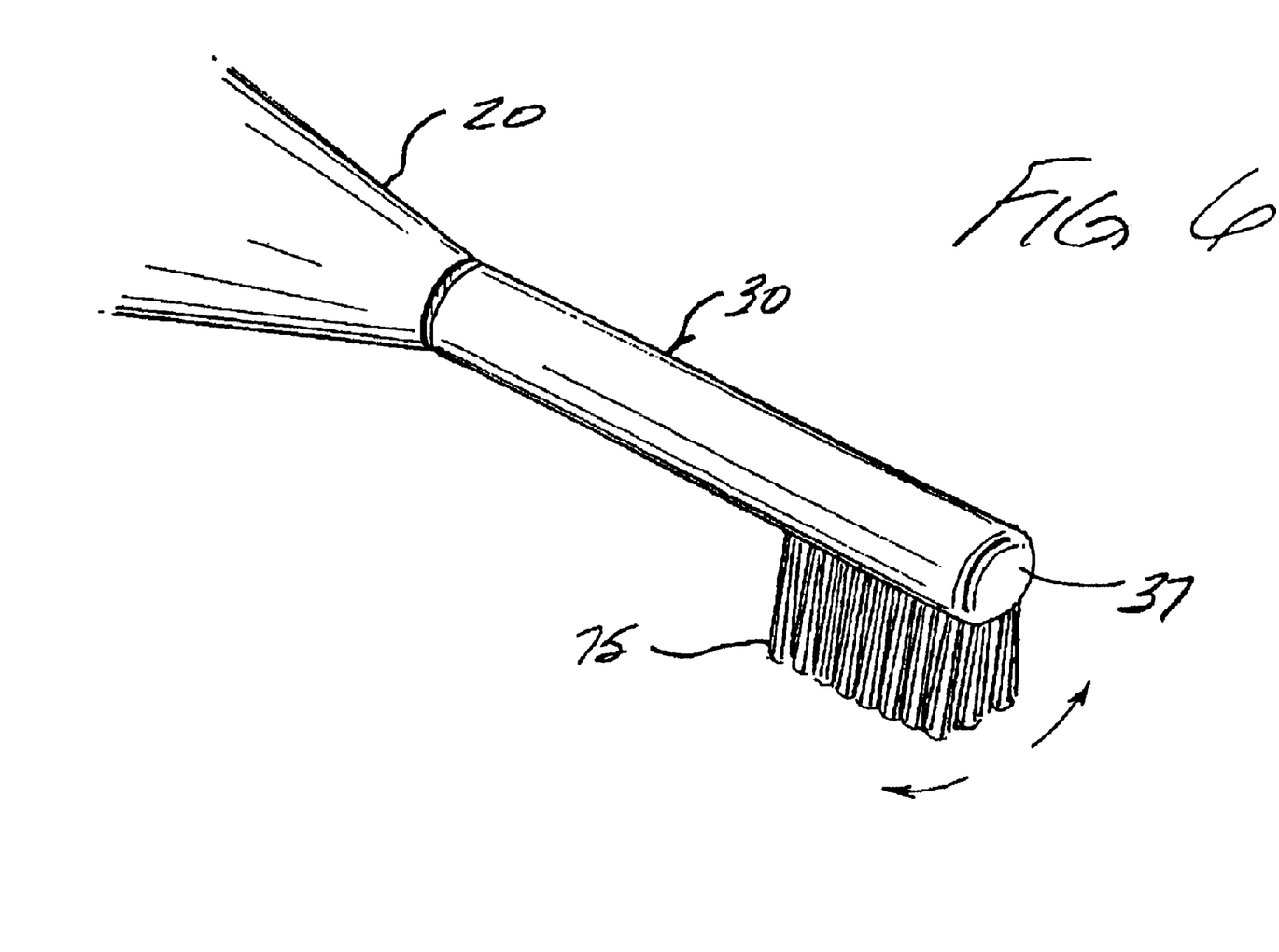
FIG. 6 is an enlarged perspective view of the distal portion of the toothbrush of FIG. 1.
Figure 7:
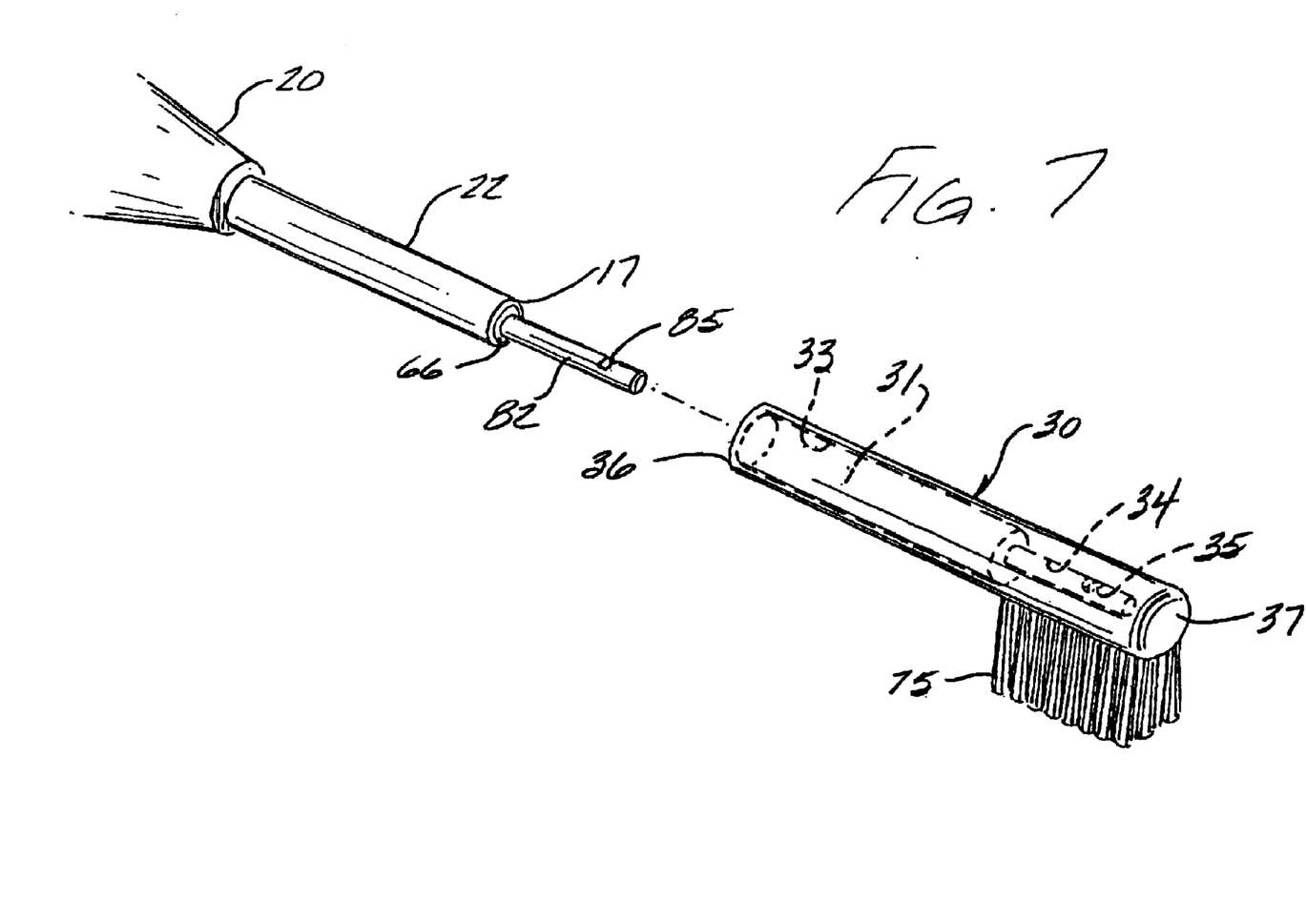
FIG. 7 is an enlarged, exploded perspective of the distal portion of the toothbrush of FIG. 1.
Figure 8:
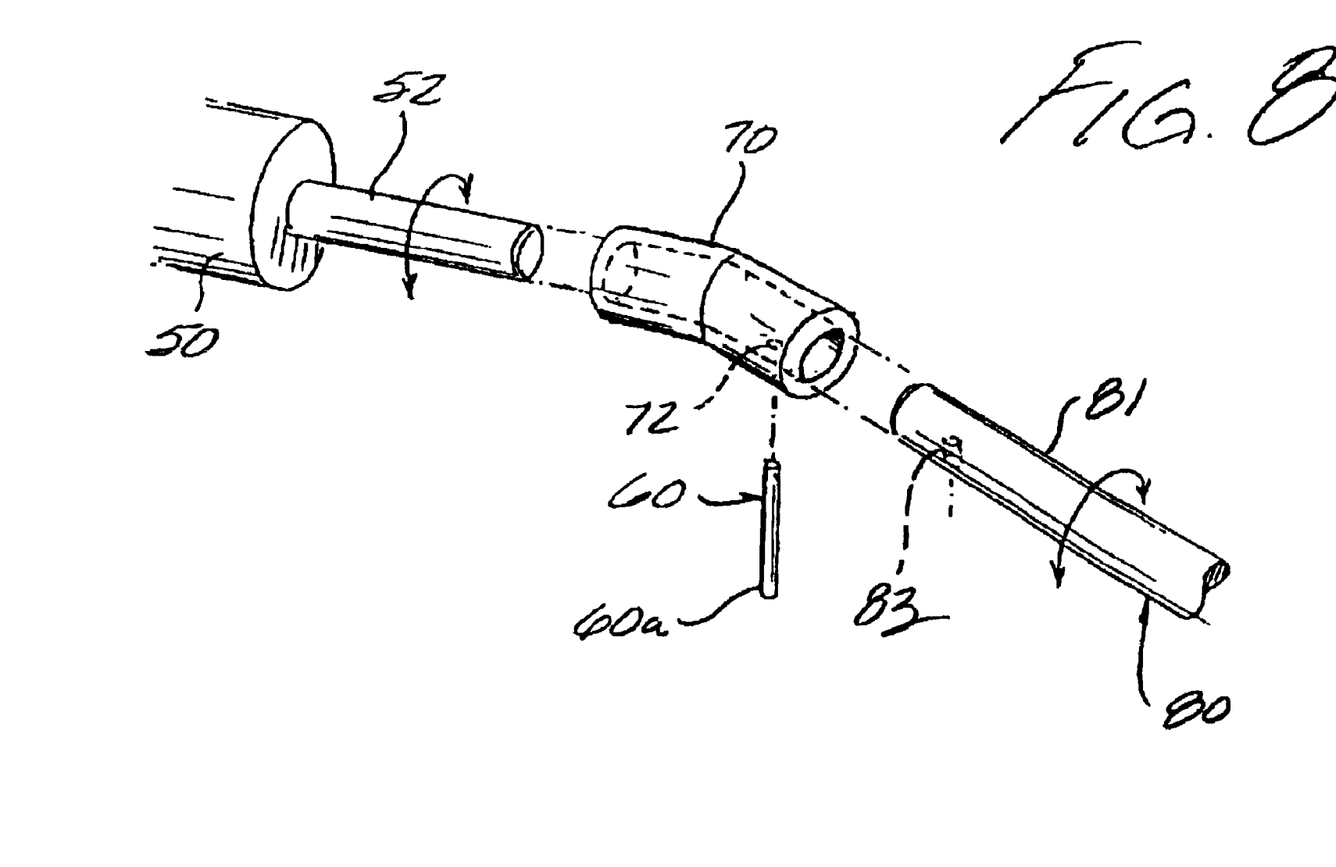
FIG. 8 is an enlarged, exploded perspective showing a flexible coupling means for connecting the output shaft of the stepper motor to a connector which, in turn, is connected to the elongate housing body.
Figure 9:
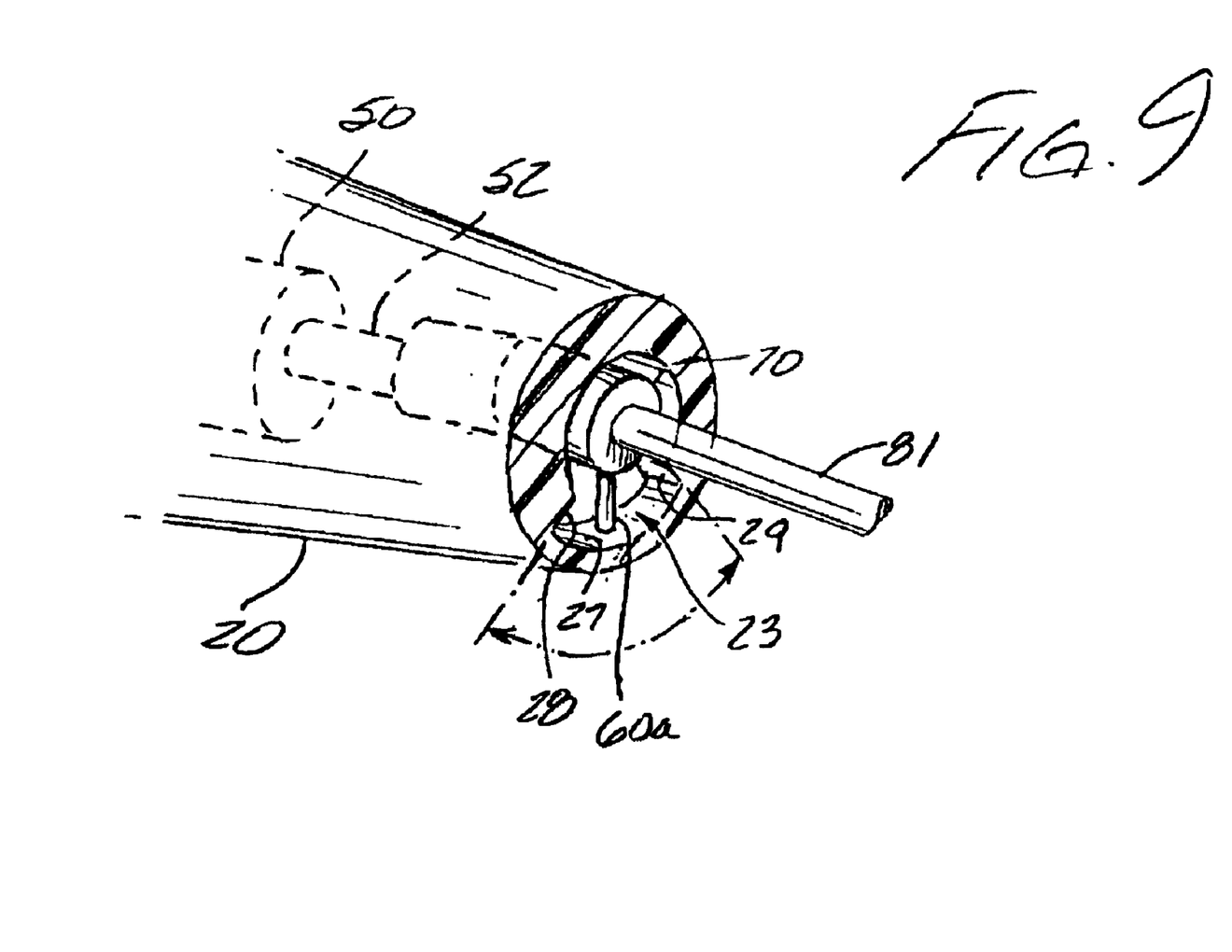
FIG. 9 is a detail view showing a stopper mechanism for use with toothbrushes according to the present invention.

Power toothbrushes in accordance with the teachings of the present invention may further include means for insuring that the desired rotary oscillating motion of the stepper motor output shaft is achieved when the toothbrush is turned on or is maintained in the event that excessive force is applied to the teeth during use of the toothbrush. The aforementioned means for insuring that the desired rotary oscillating motion of the stepper motor output shaft is maintained are illustrated in the drawings, especially FIGS. 3 and 8 thereof. FIG. 3 is a cross-sectional view taken along line 3—3 of FIG. 2B. As seen in FIG. 8, connector 70 is a piece of flexible tubing comprising rubber, silicone or the like material. One end of the flexible tubing is securely engaged, e.g. by friction fit or by use of a suitable adhesive, to the distal portion of output shaft 52 while the other end of the tubing is securely engaged to the proximal portion 81 of connecting shaft 80. A pin 60, which can be made, e.g., from metal or a suitable plastic is inserted through an aperture 72 in flexible connector 70 and thence into a blind hole 83 formed in proximal portion 81 of shaft 80. A portion 60a of pin 60 extends beyond the outer surface of flexible connector 70 as illustrated in FIG. 3 and FIG. 9. As illustrated in FIG. 3 and FIG. 9, a region of the interior wall 20a of tapered neck portion 20 is cut away to provide a slotted region 23 defined by a floor 27 and side wall portions 28 and 29. It will be seen, especially by reference to FIGS. 3 and 9, that portion 60a of pin 60 extends into the aforementioned slotted region. During normal operation, portion 60a of pin 60 travels the same path of rotary oscillating motion as that traveled by output shaft 52. In so doing, portion 60a of pin 60 alternately approaches, but does not quite contact, side walls 28, 29. At start-up, or in the event excessive force is applied during use, it is possible the controller may undesirably direct motor 50, and hence its output shaft 52, to travel to a position outside the intended or desired sweep angle. In such event, pin portion 60a will come into contact with one or the other of walls 28, 29, thus establishing maintaining the mechanism in its intended path of travel.

The stopper may be connected to a signal to alert the user when excessive force is being used. Alternatively, the stopper may be connected to an automatic shut-off, such that the toothbrush shuts off when excessive force is being used.

Figure 10:
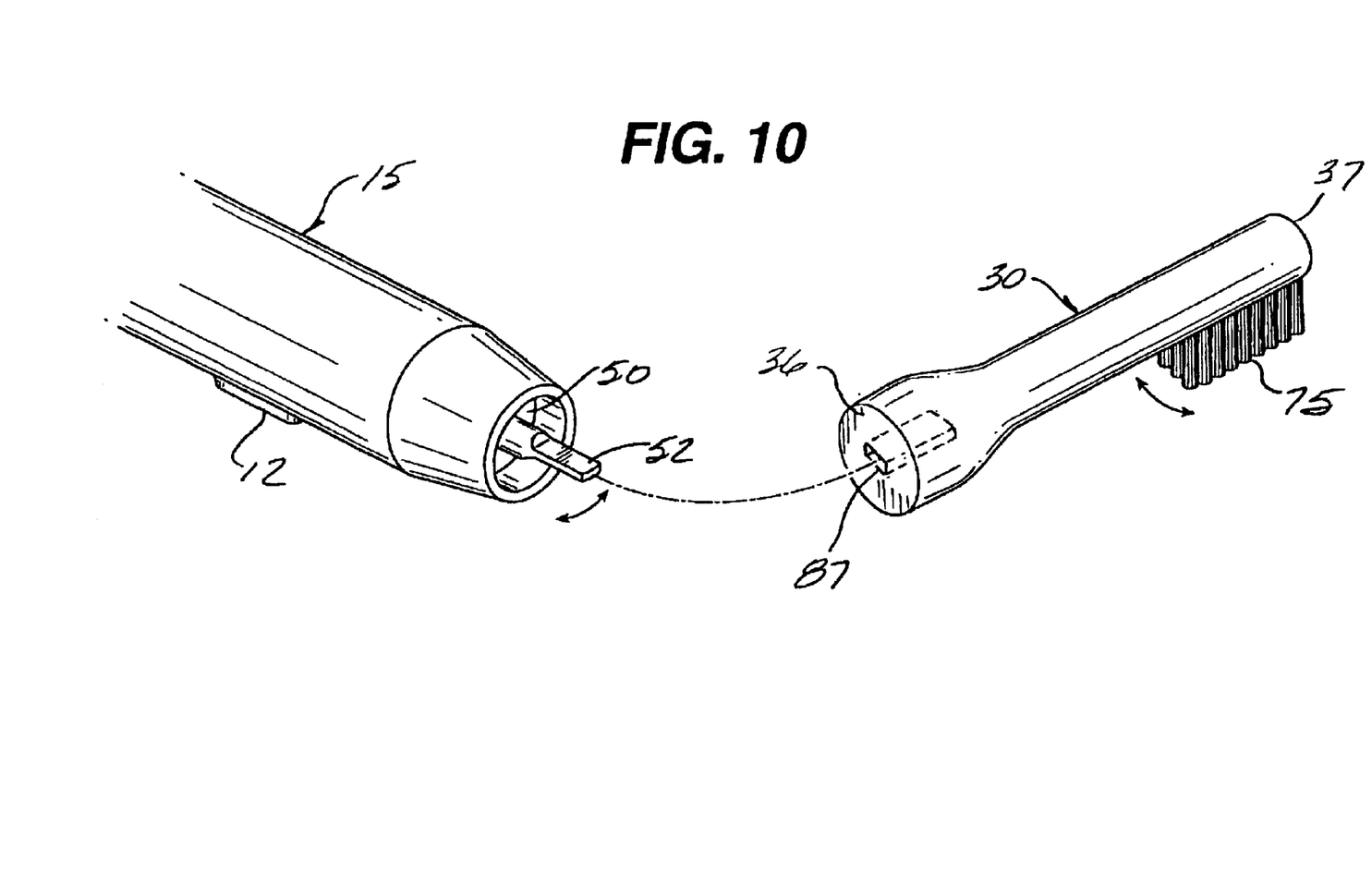
FIG. 10 is an exploded perspective of another means for connecting the output shaft of the stepper motor to the elongate housing.

Referring now to FIG. 10 of the drawings, there is illustrated a second embodiment of means for connecting elongated housing 30 to output shaft 52 of stepper motor 50. As seen in FIG. 10, the distal end of output shaft 52 has been flattened into a rectangular cross-section. Elongated housing 30 has a rectangular slot 87 formed in its proximal end 36. To assemble, the rectangularly formed distal end of shaft 52 is aligned with, then inserted into, rectangular slot 87 of housing 30. The distal end of shaft 52 can be positively retained in slot 87 by a friction fit or by other mechanisms well known in the art for achieving such retention. It will be understood that, in this embodiment, the elongated housing comprising the toothbrush bristles is connected directly to the output shaft of the stepper motor and the path traveled by the bristles during use of the toothbrush corresponds to the path traveled by the output shaft.

EXAMPLES

An example is set forth below to further illustrate the nature of the invention and the manner of carrying it out. However, the invention should not be considered as being limited to the details thereof.

Example 1

Figure 1:
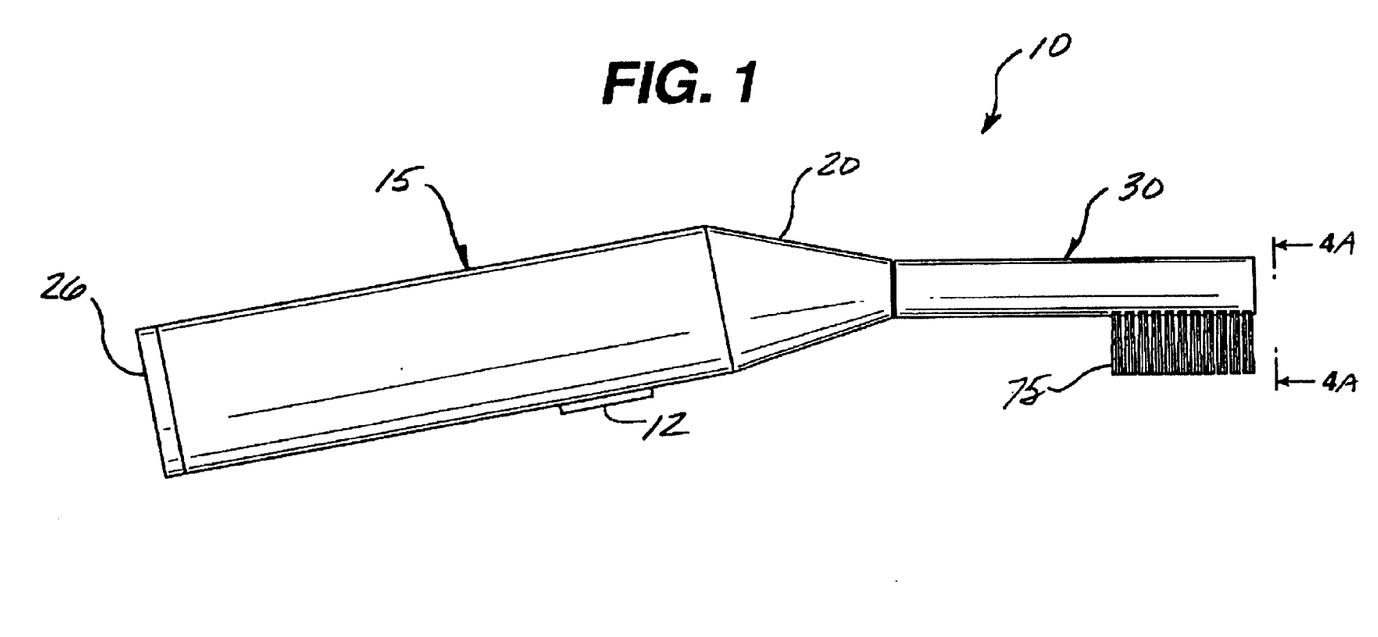
FIG. 1 is a side elevational view of one embodiment of a toothbrush in accordance with the present invention.

A power toothbrush according to FIG. 1 was made utilizing a Compmotor stepper motor (model 71-006893-01). The stepper motor was driven by a Microstep AX series computer, available through Compumotor, INC. The controller was programmed for various frequencies and angles of deflection utilizing XWARE 5.1 software, available from Compumotor, INC. The power toothbrush was hooked up to a laboratory test apparatus for determining efficacy at cleaning teeth. The apparatus and test method are described in "Access to interproximal tooth surfaces by different bristle designs and stiffness of toothbrushes", Nygaard-Ostby et al., Scand. J. Dent Res. 1979, 87, 424–430. A standard commercially available toothbrush head was attached to the power toothbrush for the test. The power toothbrush was demonstrated to be efficacious at cleaning the teeth and in between the teeth at various frequencies and angles of deflection.

We claim:

1. A power toothbrush comprising:

an elongate body defining a handle and having an interior cavity formed therein, said elongate body having a distal end and a proximal end;

an elongate housing having a proximal end and a distal end, said housing including a plurality of bristles at its distal end;

a stepper motor disposed within the interior cavity for the elongate body, said stepper motor including an output shaft providing rotary oscillating motion; and means for operatively connecting said elongate housing to the output shaft of said stepper motor.

* * * * *